United States Patent [19]

Kukreja et al.

[11] Patent Number: 5,280,038
[45] Date of Patent: Jan. 18, 1994

[54] HISTIDINE AS A PROTECTIVE AGENT IN CARDIAC SURGERY AND MYOCARDIAL ISCHEMIC SYNDROME

[75] Inventors: Rakesh C. Kukreja, Richmond; Michael L. Hess, Midlothian, both of Va.

[73] Assignee: Virginia Commonwealth University, Richmond, Va.

[21] Appl. No.: 851,203

[22] Filed: Mar. 13, 1992

[51] Int. Cl.$^5$ .................. A01N 43/50; A61K 31/415
[52] U.S. Cl. .................................................... 514/400
[58] Field of Search .......................................... 514/400

[56] References Cited

PUBLICATIONS

Rakesh C. Kukreja et al., "Singlet Oxygen Interaction with . . . ", Abstracts of the 63rd Scientific Session. 1990.

Niall MacFarlane et al., "Rapid Communication Synergism of Histidyl . . . ," J. Moll Cell Cardiol, 23, pp. 1205-1207. 1991.

Karen P. Burton et al., "Alterations in Membrane Phospholipids . . . ", Kluwer Publishers, (1988).

Roberto Bolli et al., "Role of Oxy-Radicals in Postischemic Myocardial . . . ", Kluwer Publishers (1988).

Myung-Suk Kim et al., "O$_2$ Free Radicals: Cause of Ischemia-reperfusion . . . ", Am. Psy. Soc., 0388-6135/1987.

CA 94(6):363498, Bretschneider et al., Protective solutions for heart and kidneys 1980.

*Primary Examiner*—Marianne M. Cintins
*Assistant Examiner*—Rebecca Cook
*Attorney, Agent, or Firm*—Whitham & Marhoefer

[57] ABSTRACT

Histidine has been found to be efficacious in preventing ischemic/reperfusion induced myocardial injury both functionally and ultrastructurally. Isolated perfused rat hearts (n=8/group) were subjected to 30 minutes of global ischemia and 20 minutes of reperfusion. Histidine concentrations ranging from 10 to 50 mM were given throughout the experiment. During ischemia and reperfusion without histidine the contractile function and coronary flow were 59±10% and 78±6% of control, respectively. Perfusion with histidine (25 mM and above) resulted in significant increases in contractility (94±4%) and coronary flow (92±4) levels. The incidence of arrhythmias (ventricular tachycardia and ventricular fibrillation) during reperfusion was 100 percent (8/8) in the ischemic/reperfused group with an average duration of 13.23±4.48 min. The addition of 25 mM histidine to the perfusion medium reduced the incidence and duration of arrhythmias significantly (mean±SEM 2.25±0.98 min) (P<0.01). The protective effects of histidine (25 mM and 50 mM) were significantly better than SOD/catalase/mannitol. Histidine has also been found to significantly reduce the infarct size and the occurrence of arrhythmias in vivo.

4 Claims, 15 Drawing Sheets

HISTIDINE AS A PROTECTIVE AGENT IN CARDIAC SURGERY AND MYOCARDIAL ISCHEMIC SYNDROME

BACKGROUND OF THE INVENTION

1. Field of the Invention

The present invention generally relates to coronary heart attacks and cardiac surgery. More particularly, the invention is related to the use of histidine as a protective agent during cardiac surgery and during the ischemia/reperfusion phases of acute myocardial infarction (coronary heart attack).

2. Description of the Prior Art

Heart disease is the biggest cause of death in the Western world. There are many different forms of heart disease and disease states can develop from a number of different factors including stress, diet, tobacco use, and genetic make up of the individual. Ischemia is a heart disease condition characterized as a local anemia caused by mechanical obstruction or occlusion of the blood supply. Oxygen radicals have been implicated as important mediators of tissue injury during myocardial ischemia and reperfusion. A number of studies have shown that free radicals, particularly superoxide anions ($.O_2$) and hydroxyl radicals are generated following reperfusion of the ischemic myocardium and have linked the free radical generation to the loss of contractile function. Superoxide anion is relatively unreactive and is considered dangerous because its dismutation results in the formation of hydrogen peroxide which can potentially generate the highly reactive hydroxyl radical ($.OH$) in the presence of transition metal ions. It is therefore generally believed that ultimate tissue damage occurs due to $.OH$ radicals. Indirect proof for the involvement of $.OH$ radicals in ischemia/reperfusion injury is derived from observations of a protective effect of $.OH$ radical scavengers such as dimethylthiourea (DMTU), dimethylsulfoxide, and mannitol. In addition, certain agents which prevent the formation of hydroxyl radicals have also demonstrated a protective effect including deferoxamine, superoxide dismutase (SOD), and catalase.

Another active oxygen species is singlet molecular oxygen ($^1O_2$). Singlet oxygen is not a radical; rather, it is an electronically excited state of oxygen which results from the promotion of an electron to higher energy orbitals. In Kukreja et al., *Biochim. Biophys. A*, 990:198-205 (1990), and Kukreja et al., *Am. J. Physiol.*, 259:H1330-H1336 (1989), data was presented which demonstrated that superoxide anion or hydrogen peroxide are the least reactive species in damaging sarcolemma or sarcoplasmic reticulum. Therefore, it might be inferred that the only species believed to be injurious in myocardial tissue is $.OH$ radical. However, $.OH$ radical can initiate lipid peroxidation which can produce lipid free radicals that may become important sources of singlet oxygen in vivo. Hence, the damage often attributed to the $.OH$ radical could be the resultant effects of other reaction intermediate products, including lipid free radicals and singlet oxygen.

Janero et al., *J. Mol. Cell Cardiol.*, 21:1111-1124 (1989), showed that α-tocopherol provides cellular protection by acting as a chain breaker in the lipid peroxidation process, not by scavenging the $.O_2^-$ radical per se. Singlet oxygen is also acted upon by α-tocopherol. Hearse et al., *Circ. Res.*, 65:146-153 (1989), and Vandeplassche et al., *J. Mol. Cell Cardiol.*, 22:287-301 (1990) (abstract) showed that $^1O_2$ generated from exogenous sources is able to mimic ischemia/reperfusion induced myocardial damage. Tarr et al., *J. Mol. Cell Cardiol.*, 21:539-543 (1989), recently reported that rose bengal, when applied extracellularly to frog atrial myocytes, induced a prolongation followed by a reduction of action potential duration. In addition, Donck et al., *J. Mol. Cell Cardiol.*, 20:811-823 (1988) reported that isolated myocytes exposed to rose bengal light rapidly round up and experience ultrastructural injury.

In Kukreja et al., *Abs. of 63rd Sci. Sess. (AHA) (Dallas)*, 1068 (1990), it was reported that singlet oxygen generated from photosensitization of rose bengal induced significant inhibition of calcium uptake and $Ca^{2+}$-ATPase activity in isolated sarcoplasmic reticulum. This damage caused by singlet oxygen could be significantly reduced using histidine, but not SOD or catalase. Misra et al., *J. Biol. Chem.*, 265-15371-15374 (1990), reported that histidine is a scavenger of singlet oxygen. In contrast, SOD and catalase are scavengers of superoxide anion. Kim et al., *Am. J. Physiol.*, 252:H252-H257 (1987), demonstrated histidine provides significant protection of sarcolemmal $Na^+K^+$-ATPase activity following ischemia/reperfusion in guinea pig hearts.

Electrocardiography is a well known technique for examining the condition of the heart. There are four chambers in the human heart. In operation, the right atrium receives venous blood from the body and pumps it into the right ventricle which pumps the blood through the pulmonary network where the blood becomes oxygenated by the lungs. The oxygenated blood is returned to the left atrium and is pumped into the left ventricle. The left ventricle is the most powerful chamber of the heart and serves the function of propelling the blood throughout the body network. Typically, 2,000 gallons of blood a day are pumped through the heart of a normal individual, and the heart keeps this pace throughout the life of the individual (e.g., seventy years or more). An electrocardiograph apparatus enables doctors to monitor electrical changes in the heart muscle. All the functions of the body are motivated by a complex electromechanical system which is controlled through the brain and central nervous system. Each cell within the body is surrounded by a membrane which is electrically "polarized", meaning they each have positive and negative ions on opposite sides of the membrane. Contraction of a heart muscle cell causes an electrical current flow due to the positive and negative ions. Because all of the heart cells are intimately connected, the heart organ acts as one very large cell. In the resting state (diastole), no current flows; however, as the heart expands and contracts, electrical current flows and can be sensed by electrodes.

Electrocardiography is the process of sensing and analyzing the current flow in the heart of a patient. Because the principal current detectable when a patient is at rest is produced by the heart, electrodes need not be connected directly to the heart. Typically, six or more electrodes are positioned on different portions of a patient's chest to sense the electric signals from the heart. The sensed signals are recorded on a monitor or strip chart and are referred to as an electrocardiogram. The electrocardiogram is often referred to as an ECG or EKG. According to a technique developed by Willem Einthoven in 1901, points on an ECG are labelled according to a PQRSTU system. FIG. 1 shows two cycles of a normal ECG trace where the waves are labelled PQRST. The P wave represents activity in the atria and the QRST waves represent ventricular activity. The heart's action is triggered by its own built-in pacing mechanism which comprises a bundle of specialized cardiac muscle fibers known as the sino-atrial node. The P wave represents the time taken for the electrical signal to travel throughout the muscle of the atria, whereas the QRS section represents the ventricular muscle being depolarized and the T section represents the ventricular repolarization. The U section (not shown) is often not detected and its meaning is not precisely known.

The ECG trace can provide several important pieces of information about the heart. One of the most important measurements to be made from the ECG trace is the PR interval. FIG. 2 highlights the PR interval on a single heart contraction pulse as well as other well understood portions of a single ECG trace. The PR interval is a measure of the time taken for the electrical impulse to travel through the atria to another specialized muscle bundle which synchronizes the actions of the atria and ventricles. Specifically, the PR interval is a recording of the cardiac impulse traveling to the atrioventricular (AV) node and the bundle of His, and then traversing the bundle branches and Purkinje fibers. The PR interval usually lasts 0.12 to 0.21 seconds. A longer period indicates a breakdown in the smooth operation of the AV node. The QRS section should last 0.06 to 0.11 seconds and longer periods typically indicate that the ventricles are acting sluggishly and not getting their electrical impulses simultaneously. The isoelectric ST segment and upright T wave follow the QRS section and represent ventricular repolarization. The ST segment is a sensitive indicator of myocardial ischemia or injury and should be on the isoelectric line.

Arrhythmia is a condition where the heart beats with, an irregularity in the force or rhythm. FIGS. 3 through 5 contrast the ECG of a normal sinus rhythm with ECG found for ventricular tachycardia and ventricular fibrillation, respectively. In the normal ECG of FIG. 3, there is a regularity in the P-P and R-R cycles, where the cycles are measured as the time between P and R segments of adjacent heart pulses. In ventricular tachycardia, as shown in the ECG of FIG. 4, there is a rapid and repetitive firing of ventricular premature contractions in a row. When the ventricles contract rapidly with this arrhythmia, the volume of blood ejected into the circulation is often inadequate. This kind of arrhythmia, if left untreated, often degenerates into fatal ventricular flutter or fibrillation. In ventricular fibrillation, as shown in the ECG of FIG. 5, there is no recognizable QRS complex and an extremely irregular rhythm. In this type of arrhythmia, virtually no blood is ejected into the systemic circulation, and death will occur if no corrective action is taken.

A major concern during cardiopulmonary bypass procedures is minimizing ischemic damage to the myocardium, thereby avoiding depressed myocardial performance in the post operative period. Prolonged ischemia such as that following myocardial infarction or occurring during long-term coronary bypass procedures causes serious damage to the myocardium. It has been suggested that free radicals are involved in the patho-physiology of ischemia-induced tissue damage. During ischemia, increased reducing equivalents are produced and this may favor the production of $.O_2$ anion and other free radical species upon reoxygenation. Many and varied compounds have been reported to reduce the susceptibility of the heart to ischemia/reperfusion injury. These include agents which inhibit free radical production or facilitate their elimination. Other therapeutic agents include calcium channel blockers, prostacyclin analogs and thromboxane inhibitors, sodium channel blockers, and $\alpha$- and $\beta$-adrenergic receptor blockers. Some of these agents are effective against ischemia and reperfusion induced arrhythmias, whereas others are effective against only one or the other. Prior to this invention, there were no agents available, which abolish arrhythmias, improve contractility and protect ultrastructurally.

SUMMARY OF THE INVENTION

It is therefore an object of this invention to provide a method of using histidine in the treatment of arrhythmias including ventricular tachycardia and ventricular fibrillation.

It is another object of this invention to use histidine to protect the ultrastructure of cardiac cells.

It is yet another object of this invention to provide solutions used for heart surgery and organ transplantation which contain histidine for scavenging singlet oxygen and other compounds for scavenging superoxide and hydroxyl radicals.

According to the invention, it was hypothesized that singlet oxygen is one of the most destructive species in ischemia/reperfusion injury and that histidine, because of its singlet oxygen scavenging ability, could be advantageously used for the protection of the heart. In vitro and in vivo experiments have been conducted which show that histidine has beneficial effects in preventing ischemia/reperfusion induced contractile dysfunctions, arrhythmias including tachycardia and ventricular fibrillation, impairment of coronary flow, and ultrastructure damage.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION OF THE PREFERRED EMBODIMENTS OF THE INVENTION

Figure 1:
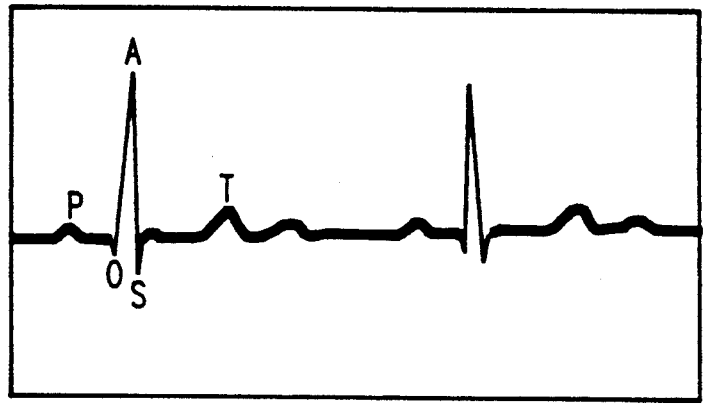
FIG. 1 is a graph showing two cycles of a normal, sinus rhythm ECG for the heart.
Figure 2:
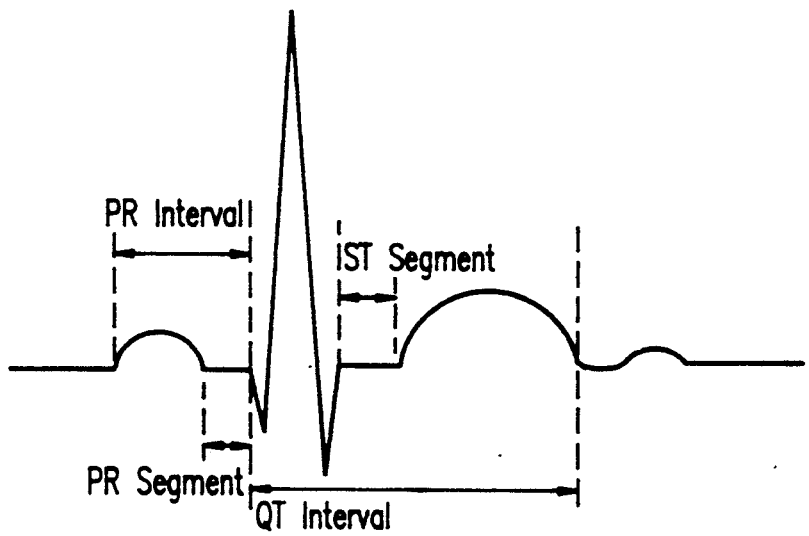
FIG. 2 is an electrical trace for a single heart beat, illustrating parts of inquiry by a cardiologist.
Figure 3:
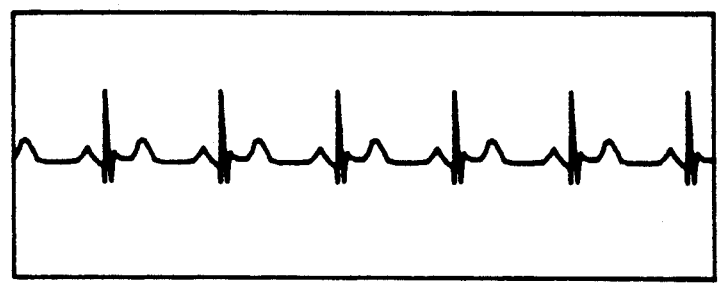
FIG. 3 is a graph showing a regular sinus rhythm ECG.
Figure 4:
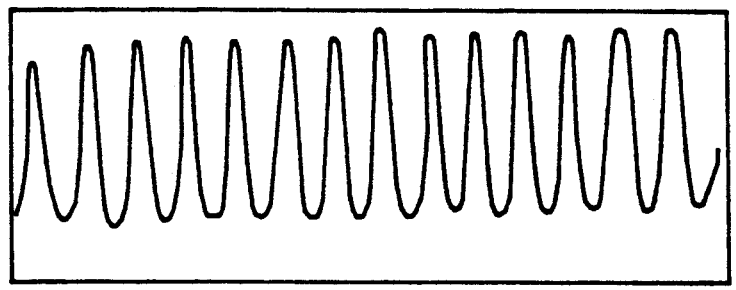
FIG. 4 is a graph showing ventricular tachycardia on an ECG.
Figure 5:
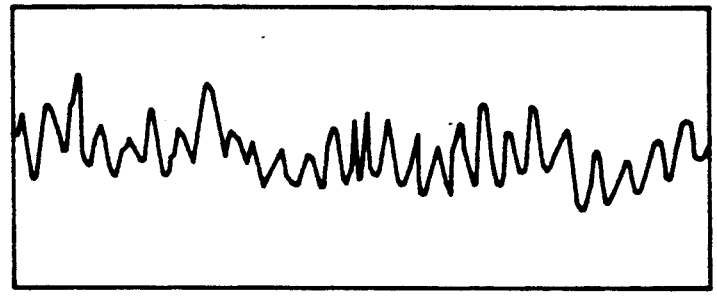
FIG. 5 is a graph showing ventricular fibrillation on an ECG.

Experiments have been conducted in vitro and in vivo which show that the histidine can be used to beneficially affect the electrical system of the heart as well as protect structural and ultrastructural components of heart cells. Specifically, the arrhythmic conditions of ventricular tachycardia and ventricular fibrillation are corrected with the addition of therapeutic quantities of histidine to the heart and the membranes of heart cell ultrastructural components are protected with the addition of histidine. It should be understood that the experimental results reported herein are provided for purposes of example and that other forms of histidine (e.g., the D-isomer, pharmaceutical salts and esters, dipeptides, and the like) could be used to achieve the beneficial effects which have been discovered.

In the in vitro experiments, male rats (250-350 gm) of the Sprague-Dawley strain were obtained from Charles River's Breeding Farms of Massachusetts. Throughout the experiments the rats were allowed ad libitum access to standard laboratory stock diet and water. In the perfusion technique, each of the animals was anesthetized with diethyl ether, and thirty seconds later, hearts with a segment of ascending aorta attached, were excised and placed in cold (4° C.) normal saline until contraction ceased (approximately 15 seconds (s)). Each heart was then cannulated through the aorta and perfused according to the method described in Langendorff, *Pfluger Arch. Physiol.*, 61:291-332 (1895), at a constant pressure of 100 cm $H_2O$. The perfusate was a modified Krebs Henseleit (KH) buffer including the following: NaCl, 118 mM; $CaCl_2$, 2.5 mM; $MgSO_4$, 1.2 mM; $NaHCO_3$, 25 mM; KCl 3.2 mM, $KH_2PO_4$ (1.2 mM) and glucose, 11.1 mM. The perfusate solution was continuously gassed with 95% $O_2$ plus 5% $CO_2$. The pH of the buffer was stable at 7.4. Histidine was directly dissolved in some of the buffer to create solutions having histidine final concentrations ranging from 10-50 mM. Some of the buffer was also combined with SOD/catalase/mannitol. All perfusion KH buffers were prepared on the day of the experiment in double-distilled deionized water.

After the excised hearts began spontaneous contraction, a small incision was made at the junction of the left atrium with the left ventricle. A latex balloon connected to a pressure transducer via a polyethylene cannula was inserted through the left atrium and mitral valve into the left ventricle. The pressure transducer was connected to a multi-channel polygraph (Grass) recorder. The balloon was inflated with water sufficient to raise the end diastolic pressure to 5 mm Hg. Coronary flow was monitored by collecting the effluent from the heart at timed intervals. An electrocardiogram (ECG or EKG) was recorded throughout the experiment via two silver electrodes attached to the ventricular apex and to the aortic cannula. In the experiments, the hearts were perfused with either the modified KH buffer alone or modified KH buffer plus histidine or SOD/catalase/mannitol. An initial thirty minute period was allowed to equilibrate rhythm and hemodynamics, and this period was followed by ischemia for 30 minutes achieved by clamping the aortic cannula. During the experiment, the heart was enclosed in an air space surrounded by a water jacket at 37° C. Reperfusion of the heart was started by opening the cannula.

In the experiments, ventricular arrhythmias were defined and quantified in accordance with the Lambeth Conventions described in Walker et al., *Cardiovasc. Res.*, 22:447,455 (1968). High speed ECG recordings were analyzed for the incidence and mean time to onset of ventricular tachycardia and ventricular fibrillation. Ventricular tachycardia was defined as a run of four or more consecutive ventricular premature beats. Ventricular fibrillation was defined as a ventricular rhythm with no recognizable QRS complex, in which signal morphology changed from cycle to cycle, and for which it was impossible to estimate heart rate.

Immediately following reperfusion, hearts with the canula still intact were taken from the Langendorff apparatus and placed in cold saline on ice. The cannula was then fitted to a perfusion pump and 1% glutaraldehyde and 1½% paraformaldehyde in 0.1M Na cacodylate at pH 7.4 was perfused retrograde (approximate speed of 10 ml/min) for three minutes. The fixative was then switched to 3% glutaraldehyde and 1½% paraformaldehyde in the same buffer for another four minutes. The cannula was then removed from the aorta and three samples (approximately 3 mm cubes) were removed from different areas of the left ventricular wall and placed in fresh 3% glutaraldehyde and 1½% paraformaldehyde in 0.1M Na cacodylate buffer at pH 7.4. The vials were stored in the refrigerator until they were processed for transmission electron microscopy (at least overnight). The samples were then cut into smaller cubes (1.5 mm) rinsed 3 times in 0.1M Na cacodylate buffer, pH 7.4 with 4% sucrose added, and postfixed for 2 hours with 2% osmium tetroxide, 0.8 % potassium ferricyanide, in 0.1M Na cacodylate on ice. The samples were rinsed with water and en bloc stained with saturated aqueous uranyl acetate for two hours at 60° C., followed by dehydration in a graded series of ethanols and then propylene oxide. Following embedding in Spurr resin, silver sections were cut from each of the samples and photographed on a JEOL EM 1200 electron microscope. Starting at the middle of the section on the left side, micrographs of each fiber were taken straight across to the right side. This is possible because one fiber usually runs the entire length of the section.

Conventional statistical methods were used to analyze the data. Student's T test for paired or unpaired comparisons were used to establish a difference between two means, and deemed significant when $p \leq 0.05$.

Preliminary studies demonstrated that normothermic global ischemia of isolated rat hearts caused a rapid decrease of the left ventricular pressure and within 6-8 minutes the hearts stopped contracting completely. In parallel to the loss of mechanical activity, an increase in the resting tension, arrhythmias, and reduction in coronary flow were also observed.

Figure 6A:
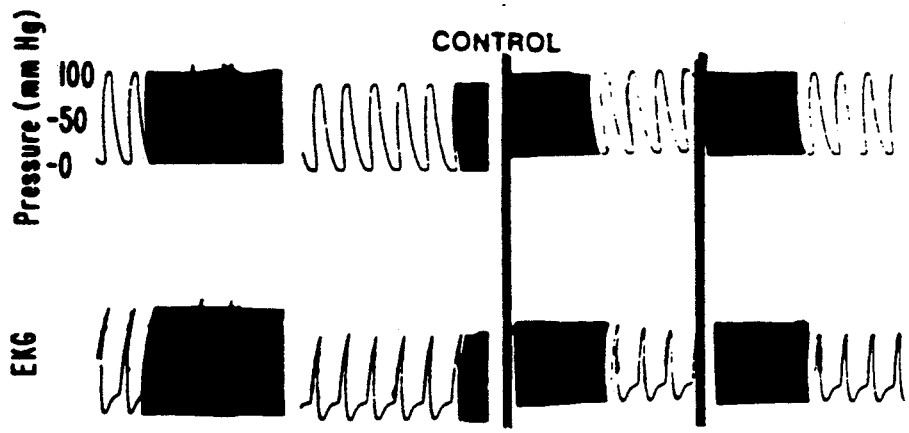
FIGS. 6a–c are graphs showing exemplary ECG and ventricular pressure recordings for a control heart, a heart exposed to global ischemia and reperfusion, and a heart exposed to ischemia/reperfusion with a histidine perfusate.
Figure 6B:
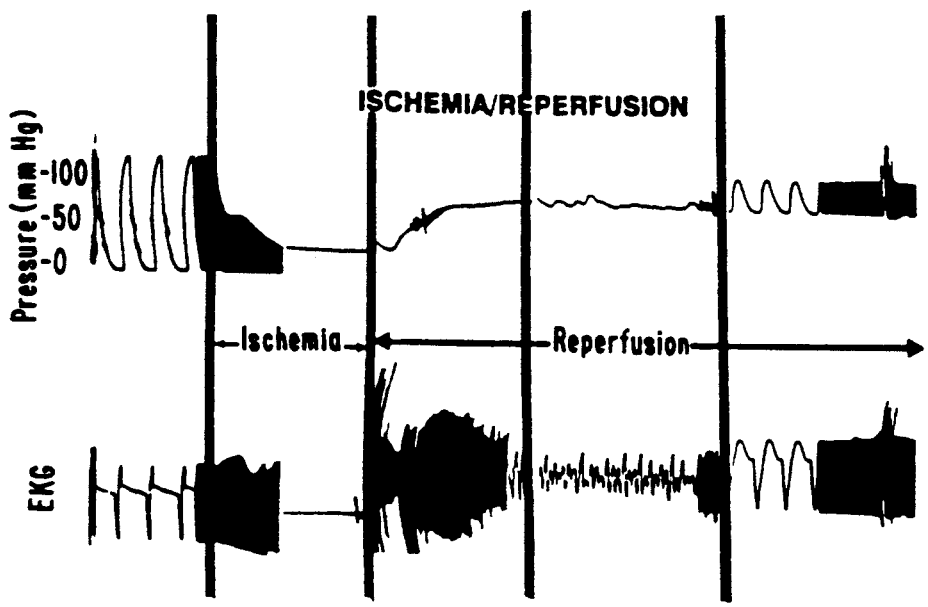
Figure 6C:
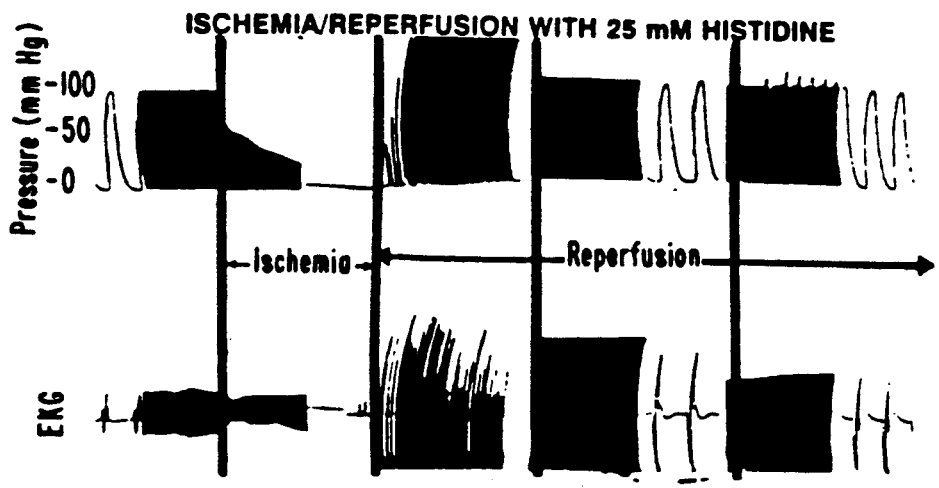

FIGS. 6a-c are exemplary EKG and ventricular pressure recordings for three different hearts. FIG. 6a shows the EKG and ventricular pressure recordings of a control heart which was not subjected to ischemia and reperfusion, while FIG. 6b and 6c show the EKG and ventricular pressure recordings of hearts subjected to thirty minutes of ischemia followed by twenty minutes of reperfusion. The hearts in FIGS. 6b and 6c were perfused throughout ischemia/reperfusion with modified KH buffer with and without 25 mM histidine, respectively. FIG. 6b shows that reperfusion of hearts without histidine after ischemia induced significant arrhythmias and that no ventricular pressure developed until after reperfusion began. In sharp contrast to FIG. 6b, FIG. 6c shows that reperfusion of hearts with 25 mM histidine resulted in the immediate development of ventricular pressure and no arrhythmias.

Figure 7:
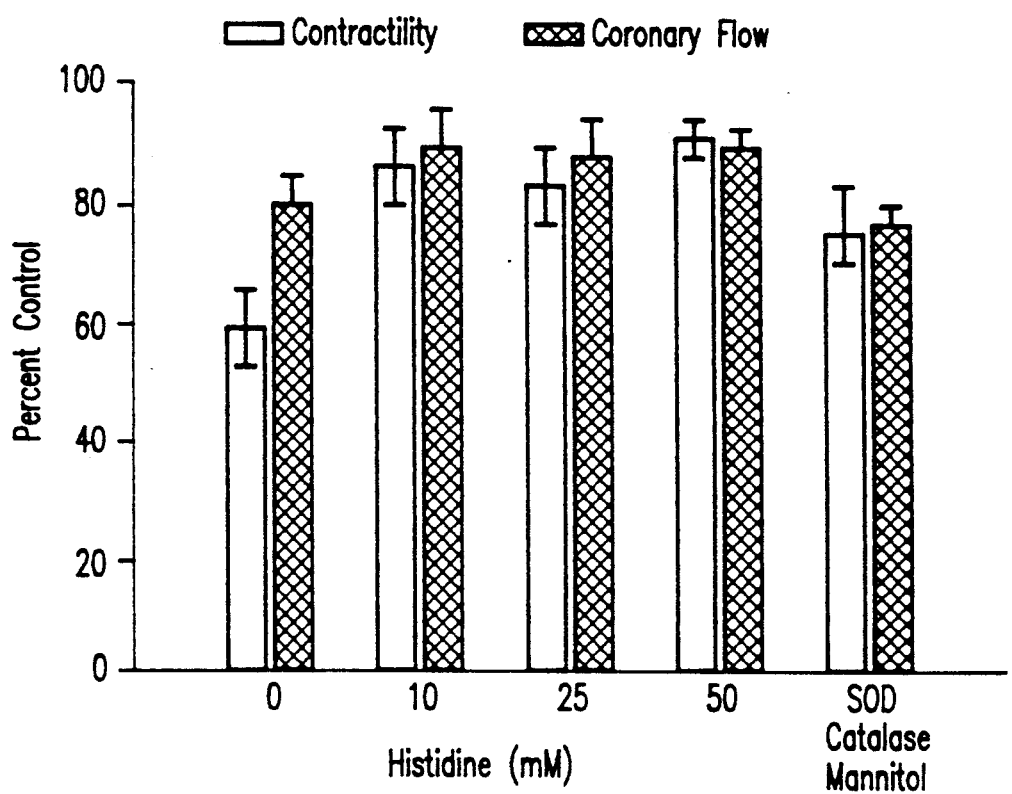
FIG. 7 is a bar graph showing the protective effects of histidine on ventricular pressure and coronary flow.

FIG. 7 shows that there is dose-dependent improvement of contractile function and coronary flow when histidine (10-50 mM) is used in the modified KH perfusate for isolated perfused rat hearts subjected to thirty minutes of normothermic global ischemia and twenty minutes of reperfusion. In ischemic/reperfused hearts, the ventricular pressure and coronary flow were $60 \pm 8$ and $80 \pm 5$ percent, respectively of a control (no ischemia) heart. Upon the addition of 10-50 mM histidine to the control modified KH buffer, there was significant improvement in the ventricular pressure and coronary flow. The protective effect of histidine was comparable to a cocktail of SOD (30 U/ml), catalase (10 μg/ml), and mannitol (20 mM) which was used as the perfusate for isolated rat hearts under the same conditions of thirty minutes ischemia followed by twenty minutes of reperfusion. Histidine was not found to interfere with the normal function of a heart which was not subjected to ischemia/reperfusion.

FIGS. 8a-e show the effect of histidine as well as the SOD/catalase/mannitol cocktail described above on ventricular tachycardia and ventricular fibrillation arrhythmias. In the Figures, each vertical bar represents the time duration of ventricular tachycardia (narrow left diagonal) and ventricular fibrillation for individual isolated and perfused rat hearts. The time of reperfusion is noted at time zero, and was begun after thirty minutes of ischemia and was continued for twenty minutes. The results for eight hearts are shown in each of the Figures.

Figure 8A:
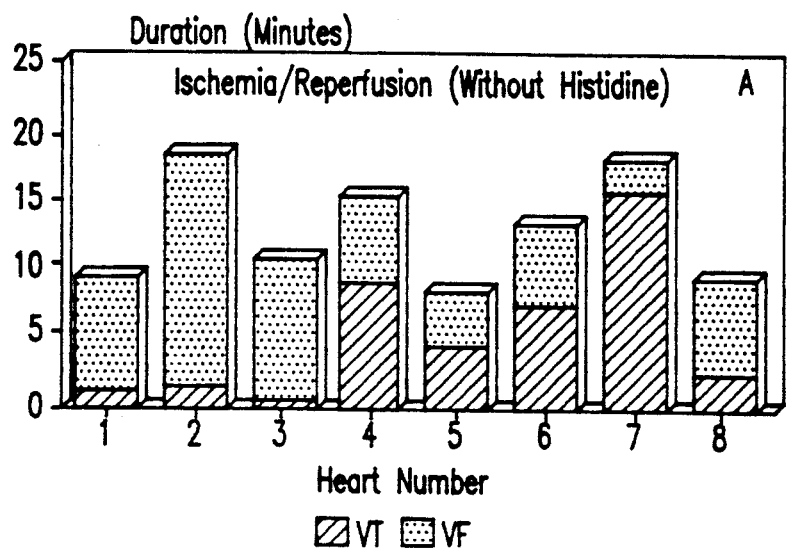
FIGS. 8a–e are bar graphs demonstrating the antiarrhythmic effects of histidine wherein a reduction in ventricular tachycardia and ventricular fibrillation was observed.
Figure 8B:
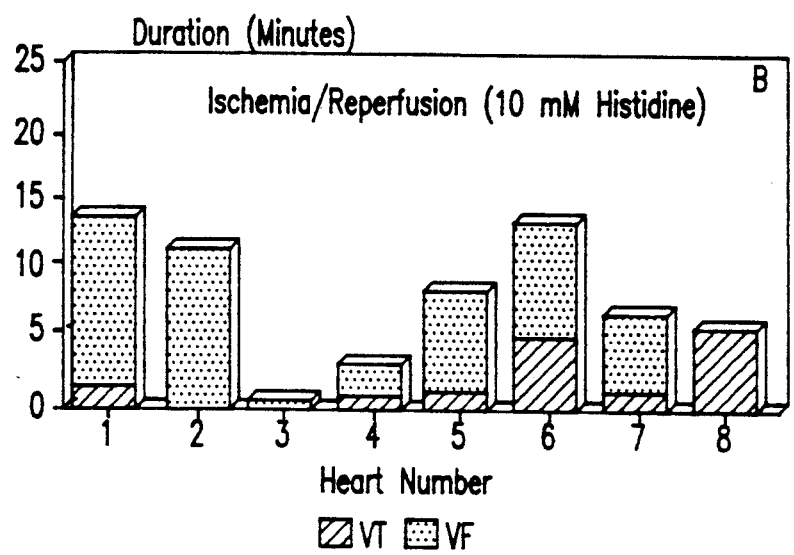
Figure 8C:
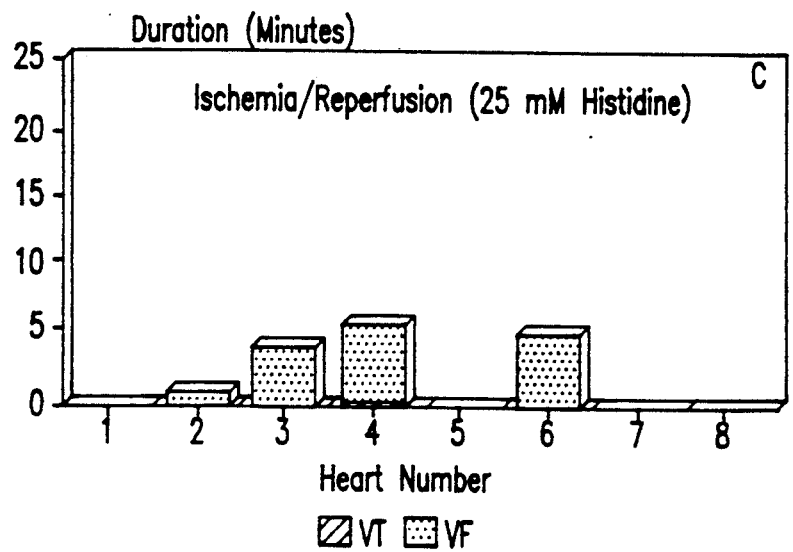
Figure 8D:
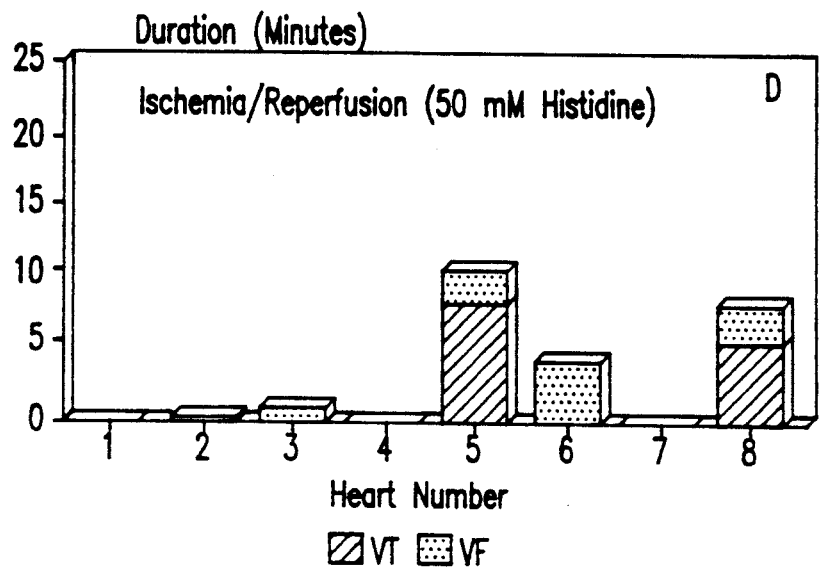
Figure 9:
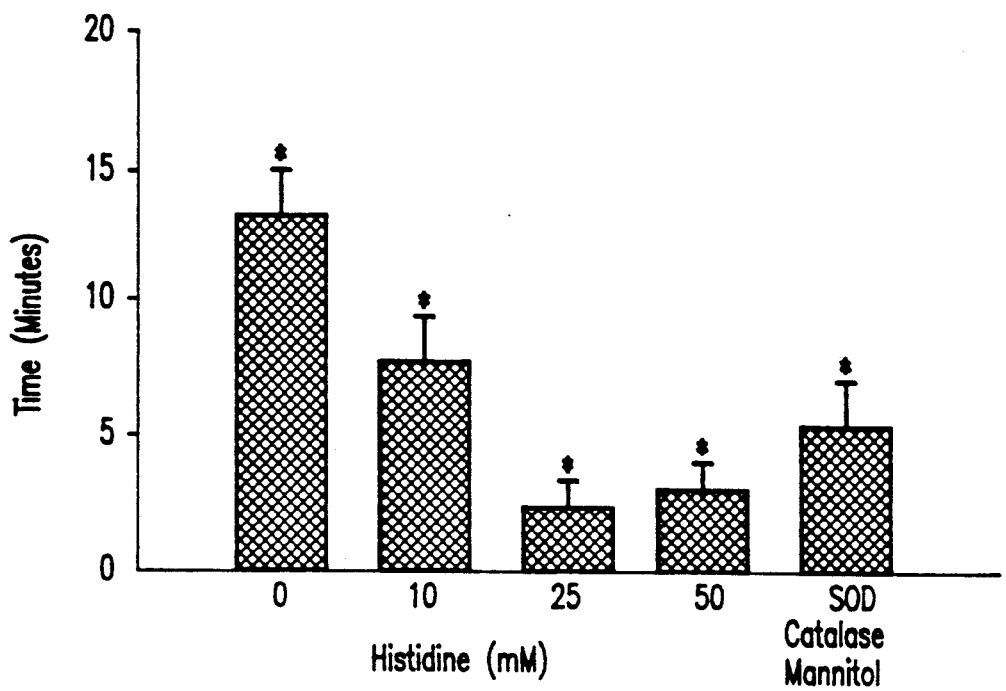
FIG. 9 is a bar graph showing the mean time for the arrhythmias observed for the eight hearts per group reported in FIGS. 8a–e.

FIG. 8a shows that ventricular tachycardia and ventricular fibrillation occurred in all eight control hearts (those in which only the modified KH perfusate was used) upon reperfusion following ischemia. FIG. 9 shows that the mean duration of the arrhythmias for the eight control hearts was $13.23 \pm 4.48$. The arrhythmias in the control hearts started almost immediately and occurred within fifteen seconds in most of the hearts. FIGS. 8b and 9 show that the hearts perfused with the modified KH perfusate which included 10 mM histidine had remarkably less arrhythmias and that the average duration of arrhythmias was significantly less (e.g. $7.56 \pm 4.94$ min.; $P < 0.01$). FIG. 8c shows that four out of eight (50%) of the hearts perfused with 25 mM histidine did not show any arrhythmias. FIG. 9 shows that the duration of ventricular tachycardia and ventricular fibrillation was $2.25 \pm 0.98$ min. for hearts perfused with 25 mM histidine which is significantly lower compared to either 10 mM histidine treated hearts or control hearts subjected to ischemia/reperfusion. FIG. 8d shows that in the 50 mM histidine treated group, in four out of eight (50%) of the hearts there was a complete absence of ventricular tachycardia and ventricular fibrillation. Moreover, in two of the remaining four hearts, there was no ventricular tachycardia observed. FIG. 9 shows that the average duration of arrhythmias in the 50 mM histidine treated group was $2.72 \pm 1.28$ min.

Figure 8E:
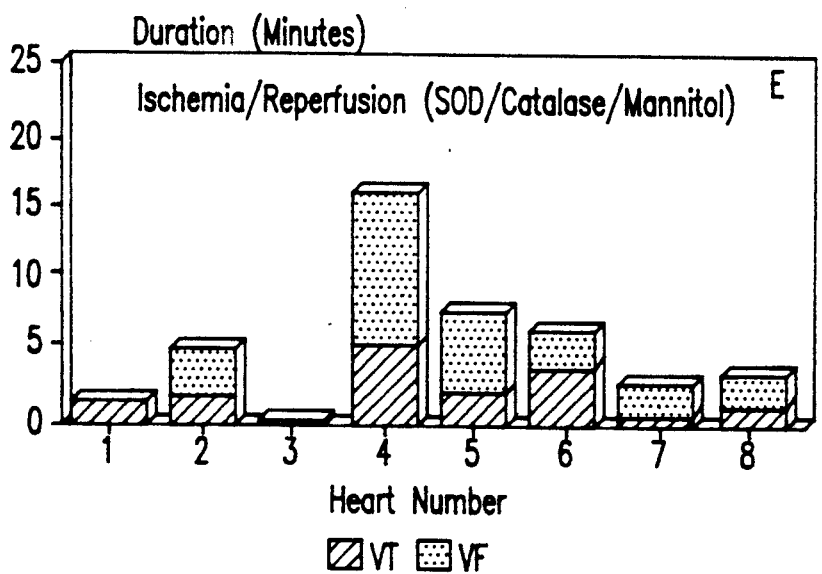

With reference to FIGS. 8e and 9, it can be seen that the hearts treated with the SOD/catalase/mannitol cocktail described above reduced the duration arrhythmias. Specifically, the average duration of arrhythmias for hearts treated with the SOD/catalase/mannitol cocktail was $5.01 \pm 1.57$ min. which is much better than the response for the control hearts and is even slightly better than what was achieved with 10 mM histidine. However, the results obtained with 25 and 50 mM histidine perfusate were clearly superior to the SOD/catalase/mannitol cocktail.

Figure 10:
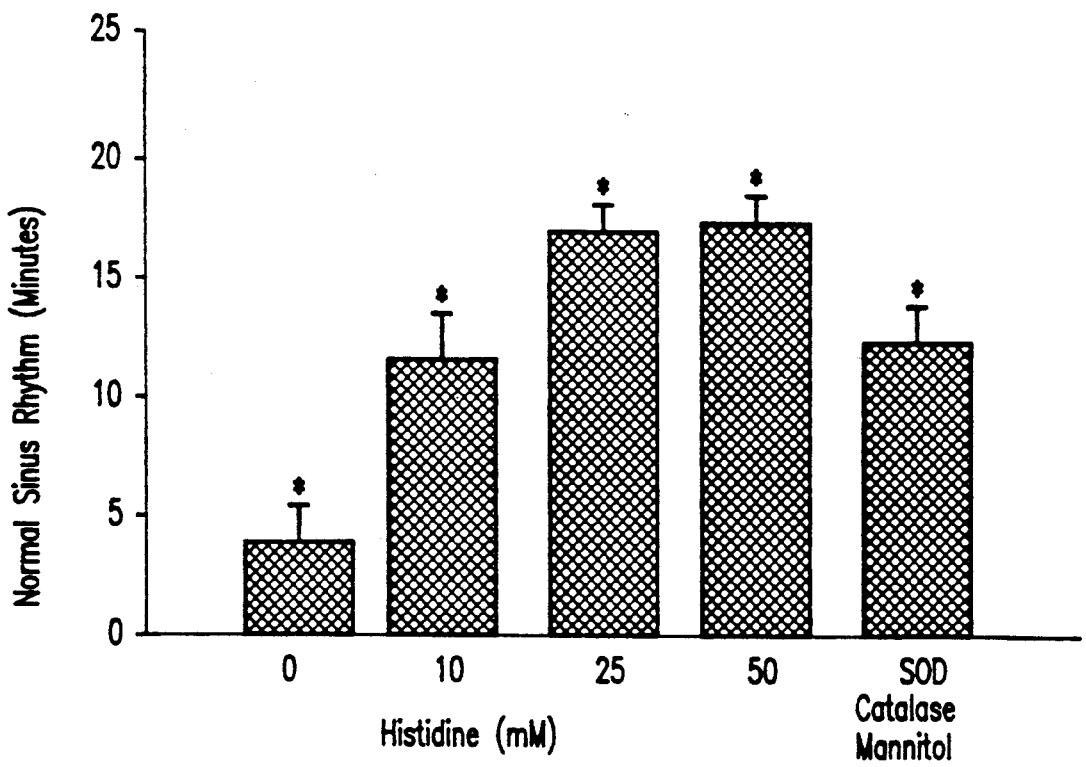
FIG. 10 is a bar graph showing the average duration of sinus rhythm during the perfusion period for the eight hearts per group reported in FIGS. 8a-e.

FIG. 10 shows the duration of normal sinus rhythm during the reperfusion period for the hearts subjected to ischemia described above in connection with FIGS. 8a-e and 9. The duration of normal sinus rhythm significantly increased following perfusion with 10 mM histidine. With 25 and 50 mM histidine, the hearts were in sinus rhythm during most of the reperfusion period. Compared to the control ischemia/reperfusion and 10 mM histidine perfused hearts, the average duration of normal sinus rhythm was significantly higher ($P < 0.05$) in 25 mM and 50 mM histidine groups. The average duration of normal sinus rhythm with the 25 mM and 50 mM treated hearts was also longer than for hearts treated with the SOD/catalase/mannitol cocktail.

FIGS. 11a-e are SEMs of heart tissues for a control heart not subjected to ischemia/reperfusion, a control heart subjected to ischemia/reperfusion where no additives were added to the modified KH perfusate, a heart subjected to ischemia/reperfusion and treated with a 10 mM histidine modified KH perfusate, a heart subjected to ischemia/reperfusion and treated with a 50 mM histidine modified KH perfusate, and a heart subjected to ischemia/reperfusion and treated with a cocktail of SOD (30 U/ml), catalase (10μg/ml), and mannitol (20 mM), respectively.

Figure 11A:
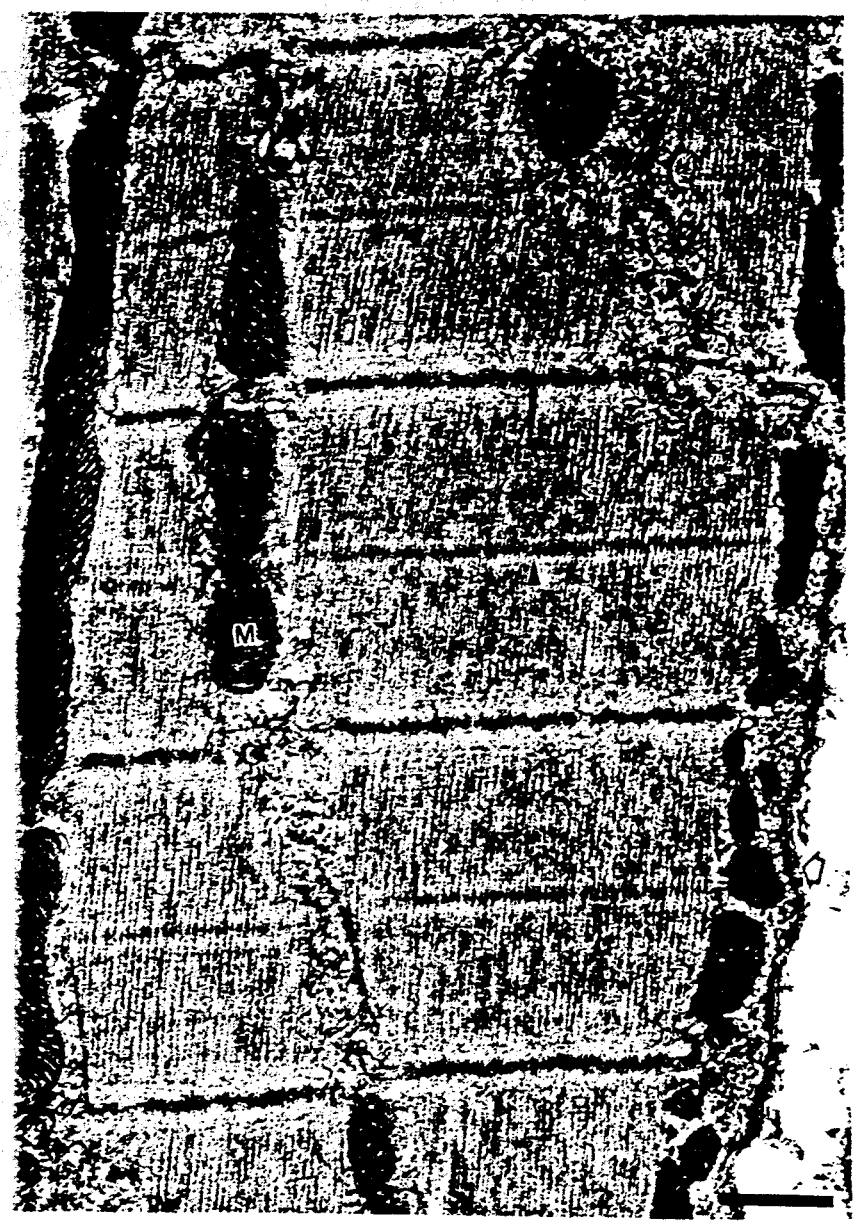
FIGS. 11a-e are scanning electron micrographs (SEMs) of portions of hearts demonstrating the ultrastructural protection of histidine.

With reference to FIG. 11a, no damage was observed in the control heart not subjected to ischemia/reperfusion. Myocytes exhibited uniform, well preserved sarcomeres and myofibrils. The Z-line and M-line were distinct and glycogen was abundant. The external lamina and associated reticular fibers were mostly intact and the mitochondria were normal. The myocardial ultrastructure was similar to that observed in normal myocardium.

Figure 11B:

With reference to FIG. 11b, some damaged cells were observed in most of the samples where the heart was subjected to ischemia/reperfusion and was not provided a protective scavenging compound. The degree of damage ranged from slightly edematous cells to severely damaged cells to an occasional necrotic cell. Several prominent changes in the damaged myocytes were seen: swelling of mitochondria, often with clearing of the matrix; the z-line was often wavy and broken; and the I-band contained globular material making the zone look "fuzzy". Other changes frequently encountered included swelling of junctional areas, depletion of cytoplasmic glycogen stores and fragmentation of sarcolemma with concurrent loss of the glycocalyx and external lamina.

Figure 11C:

With reference to FIG. 11c, it can be seen that the addition of 10 mM histidine to the perfusion medium showed evidence of protection from ischemia/reperfusion injury as judged from ultrastructural criteria. However, the mitochondria were still significantly more swollen than the control in FIG. 11a. The sarcolemma, although not discontinuous, still lacked an external lamina. There was also evidence of the same I-band "fuzziness" seen in the ischemia/reperfusion model of FIG. 11b.

Figure 11D:

With reference to FIG. 11d, it can be seen that there was very little ultrastructural damage which occurred to rat hearts treated with 50 mM histidine. The mitochondria were normal, and the sarcolemma was continuous, although the external lamina was disrupted. The sarcomeres and myofibrils were normal. The nucleus was also normal, as it was in almost all groups, and there was more glycogen present in the cytoplasm. This group had a normal appearance and was comparable to the histidine control group of FIG. 11a.

Figure 11E:

With reference to FIG. 11e, it can be seen that the SOD/catalase/mannitol cocktail added to the perfused hearts reduced ischemia/reperfusion injury as judged by ultrastructural criteria, although not as effectively as the histidine treated hearts shown in FIGS. 11c and 11d. These results correlate with the mild antiarrhythmogenic effect of these scavengers compared to the very effective antiarrhythmic properties observed with the histidine perfused hearts.

The micrographs were evaluated semi-quantitatively for myocyte damage using a 0 (indicating no damage) to 3 (indicating complete disruption) grading system for the organelles: nucleus, myofibrils, sarcolemma, mitochondria, and glycogen. Table 1 provides the grading system used in the experiments.

TABLE 1

| Gr. | Nuclei | Mitochondria | Myofibrils | Sarcolemma |
|---|---|---|---|---|
| 0 | normal; no margination or membrane disruption | normal; no swelling or dense bodies | normal; no edema or disruptions | normal; continuous membrane, glycocalyx still intact |
| 1 | slight margination and/or perinuclear edema | slight swelling, no dense bodies | I-band-Z-line fuzziness | no membrane discontinuity, but glycocalyx disrupted |
| 2 | margination, edema, and/or nuclear clearing | swollen, dense bodies and/or clumping of cristae | band fuzziness, hyper-contracted and/or edema | some membrane discontinuity, no glycocalyx |
| 3 | dense margination and nuclear clearing | all or most of above; membrane disruptions | edema, fragmentation, contraction, banding | severely disrupted membrane |

Figure 12:
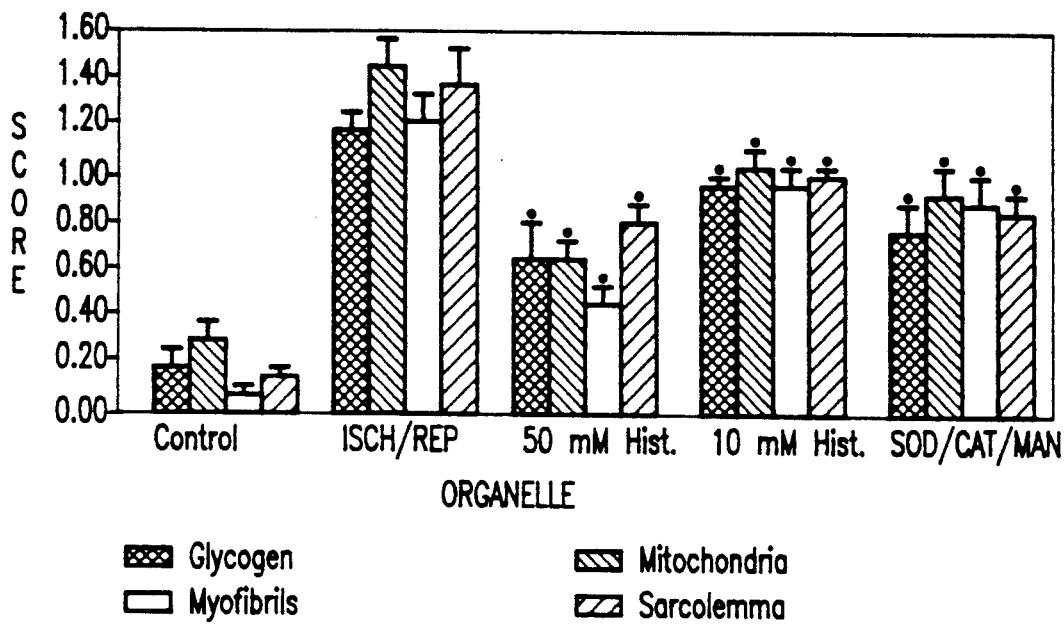
FIG. 12 is a bar graph showing semiquantitative scoring of the ultrastructural components of heart tissue treated differently during reperfusion.

FIG. 12 shows the semiquantitative data from the ultrastructural study (FIGS. 11a-e) support the qualitative observations. Specifically, 50 mM histidine provides the greatest protection from reperfusion injury. Both 10 mM histidine and the classic scavengers (SOD/catalase/mannitol) show more damage than hearts not subjected to ischemia/reperfusion, but significantly less than the ischemia/reperfusion hearts.

Figure 13:
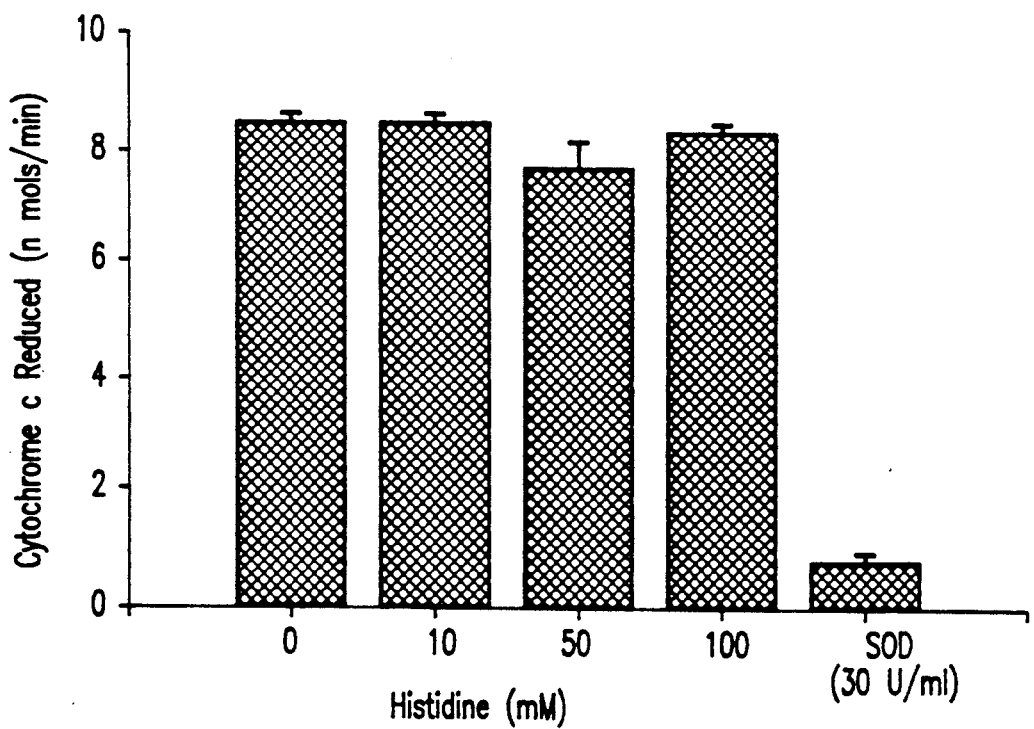
FIG. 13 is a bar graph showing that histidine does not inhibit cytochrome c reduction.

Superoxide anion is known to be produced when xanthine oxidase acts on xanthine in the presence of molecular oxygen. The $.O_2$ radicals generated can reduce ferricytochrome c. Superoxide dismutase inhibits this reaction by effectively competing with ferricytochrome c for the flux of $.O_2$. As described in McCord et al., *J. Biol. Chem.*, 243:5753-5760 (1968), this reaction has been used as a convenient assay for superoxide dismutase. When 0.005 units/ml xanthine oxidase was added to 100 $\mu$M xanthine in 0.05M potassium phosphate buffer, pH 7.8 plus $10^{-4}$ EDTA and monitored at 550 nm, a linear rate of reduction of ferricytochrome c was observed for at least five minutes with superoxide dismutase at 30 U/ml, indicating that the reduction of ferricytochrome c was dependent on $.O_2$. FIG. 13 shows that histidine at 10 to 100 mM concentrations in this model there was not significant inhibition of the rate of ferricytochrome c reduction. Therefore, histidine does not mimic superoxide dismutase. Histidine was also tested in an epinephrine autoxidation assay which produced similar results.

Exposure of cardiac sarcoplasmic reticulum to singlet oxygen generated by irradiated rose bengal showed a significant disruption of $Ca^{2+}$-ATPase activity and oxalate-supported calcium uptake into sarcoplasmic reticulum. In addition, singlet oxygen caused degradation of $Ca^{2+}$-ATPase as shown by SDS gels and HPLC. The degradation of $Ca^{2+}$-ATPase by singlet oxygen was significantly protected by histidine. Unlike singlet oxygen, $.O_2{}^-$ anion, $H_2O$, and .OH did not cause degradation of the sarcoplasmic reticulum $Ca^+$-ATPase enzyme. This suggests that the first target organelles attacked by the ischemic process is that portion of the excitation-contraction coupling system that regulates calcium delivery (the sarcolemma and sarcoplasmic reticulum) to the contractile protein and not the contractile proteins themselves.

In the in vivo studies, four groups (n=8 per group) of male Sprague Dawley rats, each having 200-250 g body weight, were anesthetized intraperitoneally with pentobarbital at 1.0 mg/kg body weight, given a tracheotomy, and ventilated with room air using a stroke volume of approximately 12 ml/kg and a rate of 55 strokes/min. Body temperature of the rats was maintained with a heated blanket. The carotid artery was cannulated to allow monitoring of arterial pressure throughout the experiment. The ECG was continuously recorded with standard limb leads. The chest was opened by a left thoracotomy and the heart was positioned external to the body. A ligature was then placed around the coronary artery close to its origin. The heart was then repositioned in the thoracic cavity. When required, the left coronary artery was occluded by snaring the artery with a small tube through which the ligature had passed. After placement of the ligature around the coronary artery, the rat preparation was allowed to stabilize for seven minutes before appropriate drug or control solution was administered. The control solution was the modified KH buffer described above and the drugs tested included both 20 mM histidine and 120 U/ml SOD. The drugs were administered to the rats intravenously at 0.5 ml in two minutes. Five minutes were then allowed for distribution of the drug. The coronary artery was then occluded and regional ischemia was maintained for fifteen minutes followed by ten minutes of reperfusion. Successful occlusion was validated in vivo by observation of a decrease in arterial pressure and ECG changes indicative of ischemia (ST segment evaluation). Reperfusion was confirmed by an increase in arterial pressure, ECG changes, and the sudden occurrence of arrhythmias, including ventricular premature beats, ventricular tachycardia, and ventricular fibrillation.

At the end of the protocol, the hearts were excised and perfused with saline through the aortic canula. The hearts were sliced transversely from apex to base in two millimeter thick sections. The left ventricle was dissected away from the right ventricle and atria and incubated in a 1% solution of triphenyltetrazolium chloride (TTC) until viable myocardium stains brick red. This identified infarcted myocardium since it fails to stain with TTC. Tissue samples were then fixed with 10% formalin solution and weighed. Color photographs of both sides of a transverse slice were then obtained. Regions possessing stained, viable and unstained, infarcted tissue were outlined on each color photograph and measured by planimetry. On each side, the fraction of left ventricle area representing infarcted tissue (average of two photographs) was multiplied by the weight of that section to determine the weight of infarcted tissue. The infarct size for each heart was expressed according to Equation 1.

$$\text{Infarct size (\%)} = \frac{\Sigma \text{ infarct weight in each slice}}{\text{Total Left Ventricle Weight}} \times 100 \quad \text{Eq. 1}$$

Figure 14:
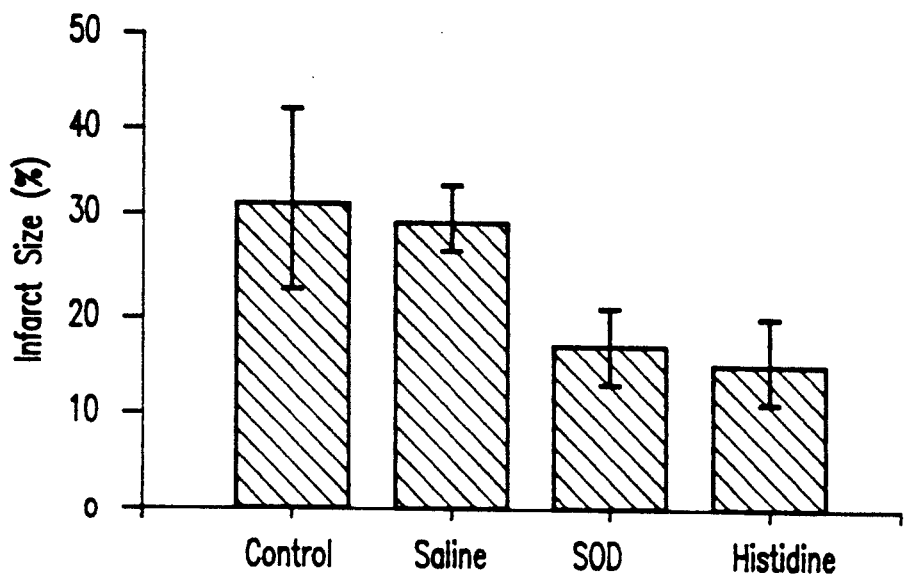
FIG. 14 is a bar graph showing the measured infarct size for rats treated with histidine in vivo.

FIG. 14 shows that the control groups which were either treated with modified KH perfusate (control group) or saline (saline group) had significant infarcts of the left ventricle wall. In addition, the control groups both displayed significant arrhythmias. The 20 mM histidine and 3000U/mg SOD treated groups demonstrated significant reductions in infarct size.

Figure 15A:
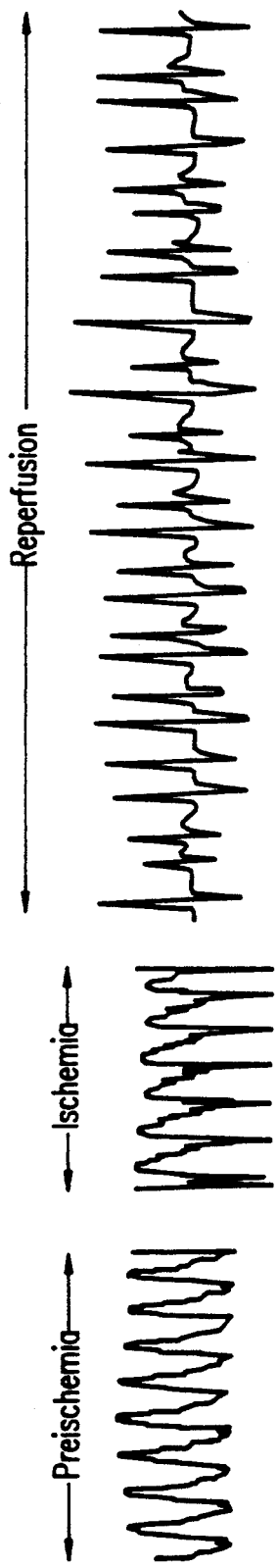
FIGS. 15a-b are ECG traces during preischemia, ischemia, and reperfusion in in situ (in vivo) rat heart preparation for a rat heart subjected to ischemia/reperfusion without histidine and a rat heart subjected to ischemia/reperfusion after prior treatment with 100 mM histidine, respectively.
Figure 15B:
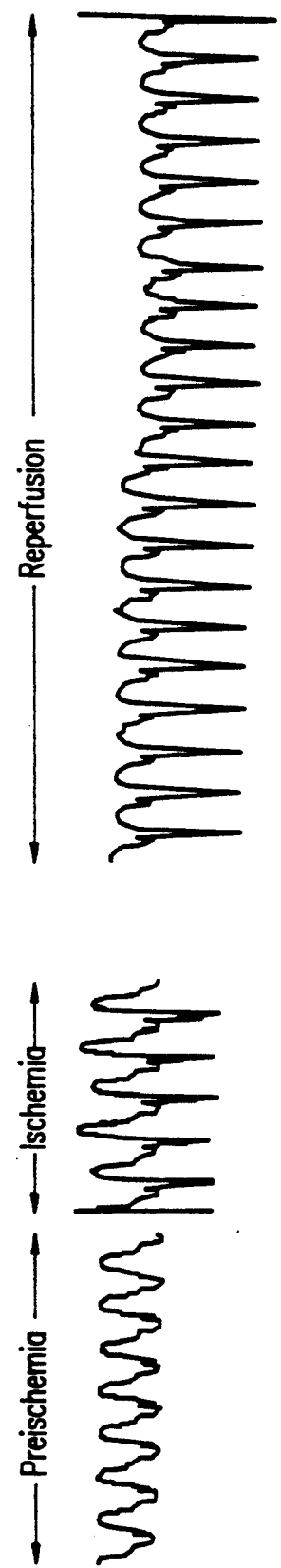

In addition, the histidine treated group showed significant reduction of arrhythmias as compared to the SOD or control groups. Contrasting FIG. 15a with FIG. 15b, it can be seen that there were significant arrhythmias during reperfusion on a control rat (FIG. 15a), whereas normal sinus rhythm existed through the reperfusion period in the 100 mM histidine treated rat (FIG. 15b). Hence, histidine has a significant protective effect against ischemia reperfusion injury in vivo.

The early diagnosis of acute or chronic myocardial ischemic syndromes is extremely crucial for myocardial salvage and patient survival. In most clinical instances, myocardial infarction and irreversible damage occurs prior to any medical or surgical procedures. The success of myocardial salvage is measured by the extent of myocardial necrosis during the ischemic episodes. The experimental results show histidine can be used during intraoperative interventions by the addition of a suitable amount of histidine (e.g., 25 mM, etc.) to cardioplegia solutions such as St. Thomas solution. During surgery, the patient would be provided an adequate oxygen supply, steps would be made to minimize intraoperative hypotension and tachycardia, adequate cooling would be provided, and preferably, a 250 mg intravenous bolus infusion of histidine would be provided to aid in managing ischemia/reperfusion injury.

The in vitro and in vivo results also show that histidine will be a very beneficial protective agent for treating patients suffering from coronary thrombosis. Ordinarily, clots are dissolved with agents such as streptokinase, TPA, APSAC, and similar thrombolytic agents. A sudden break down of the clot makes the patient vulnerable to the ventricular tachycardia and ventricular fibrillation arrhythmias discussed above. Specifically, when the patient's blood starts to flow after breaking down the clot, the situation is analogous to the reperfusion based injuries examined in the above experiments. Therefore, it would be advantageous to dose a heart attack patient with 25 mgs to 2500 mgs histidine prior to dissolving the clot with TPA, APSAC, streptokinase or other thrombolytic agents so that it can be present to scavenge singlet oxygen when the clot is broken down. In addition, it would be beneficial to combine the histidine with other free radical scavengers such as superoxide dismutase, catalase, deferoxamine, dimethylthiourea, dimethylsulfoxide, and mannitol so that any potential damage from either .OH radicals or singlet oxygen could be reduced after dissolving a clot. Furthermore, providing anticoagulative compounds such as heparin, warfarin and aspirin in combination with the histidine, superoxide dismutase, and other free radical scavengers would also be beneficial since these compounds would prevent the formation of new clots. It is anticipated that histidine could be combined with the free radical scavengers and anticoagulative compounds in a cocktail that is either administered prior to or in combination with streptokinase, tissue plasminogen activator (TPA), anixoylated plasminogen streptokinase activator complex (APSAC), or other thrombolytic clot dissolving compounds.

In addition to providing histidine during cardiac surgery or in combination with clot dissolvers used to treat coronary thrombosis, histidine might be provided by emergency technicians to patients complaining of chest pains (angina) or who have symptoms indicating a heart attack condition. In this way, a patient can be pre-dosed with histidine prior to having emergency procedures performed at an operating room. Furthermore, patients who have mild coronary thrombosis or are likely to develop coronary thrombosis may be treated with histidine on a regimented medication schedule. Because the human body has defense mechanisms which will attempt to clear a blockage, it will be important for these patients to maintain a therapeutic level of histidine in their blood to prevent arrhythmia and perform singlet oxygen scavenging when a clot is broken apart by natural mechanisms. This type of therapy is particularly applicable to patients with high cholesterol levels. As discussed at length in U.S. Pat. No. 4,920,115 to Nestler et al., an excess of low density lipoprotein (LDL) cholesterol carrier particles cause plaque build up on the interior walls of coronary arteries. High density lipoprotein (HDL) carrier particles remove excess cholesterol and, to some extent, reverse the narrowing of the artery effect by collecting cholesterol from plaque. Providing therapeutic quantities of histidine to these patients will prevent ventricular fibrillation and tachycardia if a plaque is broken apart by these natural mechanisms (e.g., breaking apart the plaque may cause the sudden reperfusion type injuries discussed in the above experiments.

Furthermore, because of the ultracellular structure protection properties exhibited in FIGS. 11a-e, it is anticipated histidine should be included in mixtures used for organ transplant purposes.

The normal level of histidine in human blood is as follows: whole blood has a histidine concentration ranging between 0.8–1.6 mg/100 ml and is on average 1.3 mg/100 ml; red blood cells have a histidine concentration in the same range as for whole blood, however, on average red blood cells have 1.1 mg/100 ml histidine; and plasma has free histidine ranging between 1.0 and 3.8 mg/100 ml. There is negligible histidine in serum.

The normal levels of histidine in human blood are far below that which has been used in the above experiments to achieve therapeutic effects. Therefore, to achieve the beneficial results in preventing ventricular tachycardia and ventricular fibrillation, as well as in protecting the ultrastructure of cardiac cells, histidine must be provided as a supplement to the patient. As in the experiments, histidine is ideally provided to a patient intravenously. Solutions could be made having 10 mM or greater concentrations of histidine which would be supplied to the patient to a therapeutic level. Normal patients will have a total of ten liters of circulating blood and ten to twenty liters of extracellular fluid. Intravenous infusion of histidine should proceed to a point where therapeutic levels in the patient's bodily fluids. It is anticipated therapeutic levels of histidine can be achieved by dosing a patient orally with tablets having 25 to 2500 mg of histidine (preferably 250 mg tablets). The tablets could be provided on a regimented schedule three to four times a day for a period prior to undergoing surgery or as a protective measure for cardiac patients. One of the principal medicines used in treating heart attack is intradermally administered nitroglycerin and it is anticipated that histidine could also be delivered intradermally to a patient. Care should be taken not to exceed toxic levels of histidine in the blood. Currently, 200 mg histidine per kilogram body weight is considered a safe upper limit for histidine concentration in the blood.

While the histidine was provided as a free base in the experiments, it could easily be provided as a salt (e.g., monohydrochloride monohydrate) or a dipeptide. The L-histidine isomer was used in these investigations. Other investigators have found beneficial effects with the D-histidine isomer; therefore, D-histidine may be preferable to L-histidine. It is anticipated that L-histidine, D-histidine and DL-histidine can be used within the practice of the invention.

Recent studies have shown that a heat-shock pretreatment improves postischemic recovery in isolated perfused heart models. This phenomenon is known as thermotolerance and seems to be mediated by a group of proteins called heat-shock proteins. Stress or heat-shock proteins were originally identified because of their increased synthesis by many cell types after exposure to elevated temperatures. A seventy kilodalton heat-shock protein was identified in neonatal and adult heart tissue of several species, including dog, rat and rabbit, and that synthesis of this protein is increased by exposure to elevated temperatures. Other stressful stimuli, such as ischemia, hypoxia, transition metals, and pressure or volume overload have also been shown to induce increased synthesis of these proteins. Closely related and identical proteins have been found in normal cells. It is now widely believed that heat-shock proteins play an essential part in normal cells and in a cells' response to stress. The common feature of the stress proteins is their ability to bind denatured or malfolded proteins during a period of stress.

Studies in different species have shown that increased heat-shock protein express may protect the heart against subsequent damage. Exposure of rats to elevated temperature, with consequent cardiac heat-shock protein induction, have resulted in improved recovery of contractile function after subsequent ischemia and reperfusion. Reperfusion damage, as measured by creatine kinase release was significantly reduced in heat-shocked hearts. The increased concentrations of heat-shock protein 70 was accompanied by increases in corresponding messenger ribonucleic acid (mRNA) and an increase in activity of the classical antioxidant enzyme, catalase.

Figure 16:
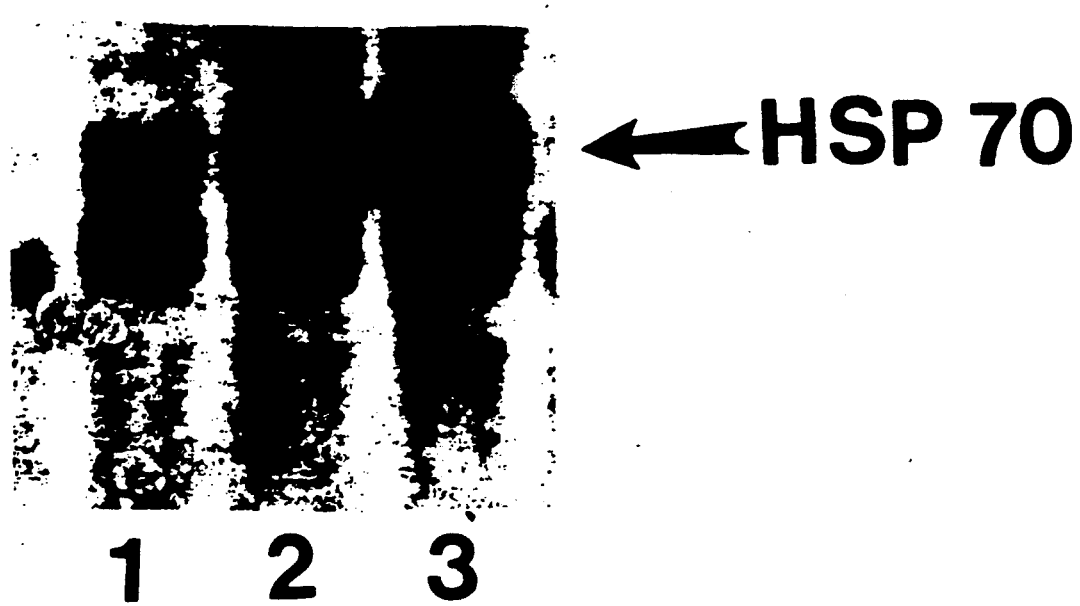
FIG. 16 is a Northern blot showing the enhanced gene expression for heat shock protein for cardiac cells treated with histidine.

FIG. 16 shows a northern blot performed on an isolated histidine perfused rat heart which had been subjected to ischemia as described above. Lane 1 denotes a control heart which was not subjected to ischemia, lane 2 denotes a heart subjected to thirty minutes of ischemia followed by twenty minutes of reperfusion, and lane 3 denotes an ischemic perfused heart with 25 mM histidine. It can be seen that the density of the heat shock protein 70 (HSP 70) band in lane 3 is higher compared to the control heart in lane 1 and the ischemic/reperfused heart (without histidine) in lane 2. Hence, histidine clearly enhances the expression of the heat-shock protein and this may be another mechanism for cardiac protection exerted by histidine (e.g., the primary method probably being that of acting as a singlet oxygen scavenger).

While the invention has been described in terms of its preferred embodiments, those skilled in the art will recognize that the invention can be practiced with modification within the spirit and scope of the appended claims.

Having thus described our invention, what we claim as new and desire to secure by Letters Patent is as follows:

1. A method of preventing or treating ventricular tachycardia and ventricular fibrillation, comprising the steps of:
   identifying a patient that is suffering from or is likely to suffer from ventricular tachycardia or ventricular fibrillation; and
   administering to said patient a sufficient amount of histidine to reduce the occurrence of ventricular tachycardia or ventricular fibrillation arrhythmias.

2. The method of claim 1 wherein said step of identifying comprises the step of removing a blockage in coronary or cardiac tissue in said patient.

3. The method of claim 1 wherein said step of identifying comprises the step of dissolving a blockage in coronary or cardiac tissue in said patient.

4. The method of claim 3 wherein said steps of dissolving a blockage and administering histidine are performed at the same time.

* * * * *